United States Patent
Gratton et al.

(10) Patent No.: US 9,790,106 B2
(45) Date of Patent: Oct. 17, 2017

(54) RADIATION SOURCE MODULE AND FLUID TREATMENT SYSTEM

(71) Applicant: Trojan Technologies, London (CA)

(72) Inventors: Richard David Gratton, St. Mary's (CA); Guang Kuan Wei, London (CA); Wesley Daniel From, London (CA)

(73) Assignee: Trojan Technologies, London, Ontario (CA)

( * ) Notice: Subject to any disclaimer, the term of this patent is extended or adjusted under 35 U.S.C. 154(b) by 0 days.

(21) Appl. No.: 15/099,022

(22) Filed: Apr. 14, 2016

(65) Prior Publication Data

US 2016/0304362 A1  Oct. 20, 2016

Related U.S. Application Data

(60) Provisional application No. 62/178,651, filed on Apr. 16, 2015.

(51) Int. Cl.
*C02F 1/00* (2006.01)
*C02F 1/32* (2006.01)
(Continued)

(52) U.S. Cl.
CPC .............. *C02F 1/325* (2013.01); *A61L 2/10* (2013.01); *C02F 2103/02* (2013.01);
(Continued)

(58) Field of Classification Search
USPC ........ 250/432 R, 435, 436, 437; 210/167.01, 210/629, 748.1, 748.11; 422/186.3, 291,
(Continued)

(56) References Cited

U.S. PATENT DOCUMENTS

| 3,634,025 A | * | 1/1972 | Landry | ..................... A61L 2/10 250/372 |
|---|---|---|---|---|
| 4,367,410 A | * | 1/1983 | Wood | ....................... A61L 2/10 250/431 |

(Continued)

FOREIGN PATENT DOCUMENTS

| CA | 2872607 | 11/2013 |
|---|---|---|
| DE | 4206596 | 9/1993 |
| WO | WO2004000735 | 12/2003 |

OTHER PUBLICATIONS

Extended European Search Report for Application No. 16164418.2, dated May 25, 2016.
(Continued)

*Primary Examiner* — Bernard Souw
(74) *Attorney, Agent, or Firm* — Michael Stanley Tomsa; McAndrews, Held & Malloy, Ltd.

(57) ABSTRACT

There is described a radiation source module for use in a fluid treatment system. The radiation source module comprises a plurality of elongate radiation source elements secured to a frame element, each elongate radiation source element having a longitudinal axis; a first motive element secured to a first side portion of the frame element; and a second motive element secured to a second side portion of the frame element. The first motive element and the second motive element are configured to reversibly translate the plurality of elongate radiation source elements in a direction substantially parallel to the longitudinal axis. A fluid treatment system comprising the radiation source module is also described.

22 Claims, 6 Drawing Sheets

(51) Int. Cl.
    *A61L 2/10* (2006.01)
    *B01J 19/12* (2006.01)
    *C02F 103/02* (2006.01)
(52) U.S. Cl.
    CPC  *C02F 2201/322* (2013.01); *C02F 2201/3225* (2013.01); *C02F 2201/3227* (2013.01); *C02F 2303/04* (2013.01); *C02F 2303/14* (2013.01)
(58) Field of Classification Search
    USPC .......................................................... 422/297
    See application file for complete search history.

(56)  References Cited

U.S. PATENT DOCUMENTS

| | | | | |
|---|---|---|---|---|
| 4,482,809 A | * | 11/1984 | Maarschalkerweerd | A61L 2/10 250/435 |
| 4,872,980 A | * | 10/1989 | Maarschalkerweerd | A61L 2/10 210/192 |
| 5,006,244 A | * | 4/1991 | Maarschalkerweerd | A61L 2/10 210/192 |
| 5,332,388 A | * | 7/1994 | Schuerch | A61L 2/10 134/104.1 |
| 5,660,719 A | * | 8/1997 | Kurtz | A61L 2/10 210/748.11 |
| 5,952,663 A | * | 9/1999 | Blatchley, III | B01J 19/123 250/435 |
| 6,500,312 B2 | * | 12/2002 | Wedekamp | C02F 1/325 210/748.11 |
| 2008/0260602 A1 | * | 10/2008 | Traubenberg | C02F 1/325 422/186.3 |

OTHER PUBLICATIONS

Office Action in Canadian Application No. 2,927,345, dated Jan. 27, 2017.

* cited by examiner

RADIATION SOURCE MODULE AND FLUID TREATMENT SYSTEM

CROSS-REFERENCE TO RELATED APPLICATION

The present application claims the benefit under 35 U.S.C. §119(e) of provisional patent application Ser. No. 62/178,651, filed Apr. 16, 2015, the contents of which are hereby incorporated by reference.

BACKGROUND OF THE INVENTION

Field of the Invention

In one of its aspects, the present invention relates to a radiation source module for use in a fluid treatment system. In another of its aspects, the present invention relates to a fluid treatment system incorporating a radiation source module.

Description of the Prior Art

Fluid treatment systems are generally known in the art. More particularly, ultraviolet (UV) radiation fluid treatment systems are generally known in the art.

Early treatment systems comprise so-called "open channel" reactors.

For example, U.S. Pat. Nos. 4,482,809, 4,872,980 and 5,006,244 (all in the name of Maarschalkerweerd and all assigned to the assignee of the present invention and hereinafter referred to as the Maarschalkerweerd Patents) describe gravity fed fluid treatment systems which employ ultraviolet (UV) radiation.

Such systems include an array of UV lamp modules (e.g., frames), which include several UV lamps each of which are mounted within sleeves that extend between and are supported by a pair of legs that are attached to a cross-piece. The so-supported sleeves (containing the UV lamps) are immersed into a fluid to be treated, which is then irradiated as required. The amount of radiation to which the fluid is exposed is determined by the proximity of the fluid to the lamps, the output wattage of the lamps and the flow rate of the fluid past the lamps. Typically, one or more UV sensors may be employed to monitor the UV output of the lamps and the fluid level is typically controlled, to some extent, downstream of the treatment device by means of level gates or the like.

The Maarschalkerweerd Patents teach fluid treatment systems that were characterized by improved ability to extract the equipment from a wetted or submerged state without the need for full equipment redundancy. These designs compartmentalized the lamp arrays into rows and/or columns and were characterized by having the top of the reactor open to provide free-surface flow of fluid in a "top open" channel. These designs were also characterized by disposing each individual elongate lamp (or elongate radiation source) such that the longitudinal axis thereof is substantially parallel to the direction of fluid flow through the open channel.

It is also known to dispose the lamps such that the longitudinal axis thereof is orthogonal to the direction of fluid flow through the open channel. For example, U.S. Pat No. 5,952,663 to Blatchley, III et al. (Blatchley) describes an apparatus for applying ultraviolet radiation dosage to fluids in an open channel. With particular reference to FIG. 12 in Blatchley, there is shown a fluid treatment channel containing a module having a series of vertically disposed lamps (14). Disposed on the sidewalls of the fluid channel are a series of fluid diverters (27). As shown, the arrangement of fluid diverters (27) is such that each fluid diverter (27) projects into the fluid treatment channel to the same extent. Such an arrangement is disadvantages since it results in relatively high fluid head loss and low treatment efficiency.

It is also known to dispose the lamps such that the longitudinal axis thereof is disposed at an oblique angle (i.e., non-parallel and non-orthogonal) with respect to the direction of fluid flow through the open channel. For example, Canadian patent application 2,872,607 to Morningstar et al. (Morningstar) describes an ultraviolet radiation (UV) water treatment plant comprising at least one module, which includes an array of elongate UV radiation lamps in a mount. The radiation lamps are disposed in parallel to one another and at an oblique angle with respect to the direction of water flow in the open channel. A base is provided to which at least one guide is fixedly connected, and at least one guide rail is provided that is connected to the mount. The guide rail is movably mounted in the guide.

The module described by Morningstar includes a serially offset base (i.e., disposed upstream or downstream of the array of elongate UV radiation lamps) having a centrally disposed mechanical lift mechanism which serves to translate the array of elongate UV radiation lamps in a direction away from the open channel for servicing, etc. A problem with this approach is that it is not possible to tightly arrange serial arrays of elongate UV radiation lamps because of the space required for the centrally disposed mechanical lift mechanism associated with each module. For example, it is not possible to arrange serial modules illustrated by Morningstar such that the distance between serial rows of elongate UV radiation lamps in an array in a single module is the same or less that the distance between rows of elongate UV radiation lamps in serially adjacent modules. The result is that the water treatment plant described by Morningstar requires a relatively large footprint of space to accommodate all necessary components. This is particularly problematic if a UV radiation water treatment system is being used to replace a conventional chlorine disinfection system.

It would be highly desirable to have a radiation source module and a fluid treatment is system that overcomes the above problems. More specifically, it would be highly desirable to have a radiation source module and a fluid treatment system that make it possible to arrange serial modules such that the distance between serial rows of elongate UV radiation lamps in an array in a single module is the same or less that the distance between rows of elongate UV radiation lamps in serially adjacent modules. This would allow for a reduction (compared to the module and water treatment described by Morningstar) in the footprint of space to accommodate all necessary components. This would be particularly advantageous if a UV radiation water treatment system is being used to replace a convention chlorine disinfection system.

SUMMARY OF THE INVENTION

It is an object of the present invention to obviate or mitigate at least one of the above-mentioned disadvantages of the prior art.

It is another object of the present invention to provide a novel radiation source module.

It is another object of the present invention to provide a novel fluid treatment system.

Accordingly, in one of its aspects, the present invention provides a radiation source module for use in a fluid treatment system, the radiation source module comprising: a plurality of elongate radiation source elements secured to a frame element, each elongate radiation source element having a longitudinal axis; a first motive element secured to a first side portion of the frame element; a second motive element secured to a second side portion of the frame element; wherein the first motive element and the second motive element are configured to reversibly translate the plurality of elongate radiation source elements in a direction substantially parallel to the longitudinal axis.

Thus, the present inventors have discovered a novel radiation source module which obviates or mitigates the above-disadvantages of the prior art.

Thus, the present inventors have discovered a novel radiation source module that obviates or mitigates the disadvantages associated with Morningstar described above. More particularly, by avoiding the need to have a centrally disposed mechanical lift mechanism associated with each module, it is possible to reduce the footprint of the modules used in the fluid treatment system. Further, because the motive elements are disposed on opposed sides of each module, the motive element can support the module and no extra guide such as that described in Morningstar is required. Still further, by placing the mode of elements in an area of the open channel which is relatively stagnant to fluid flow, the impact on disinfection performance and hydraulic head loss is minimized. The motive element can be manually driven and/or electrically drive, and it can involve the use of a winch and/or a cable.

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Figure 1:
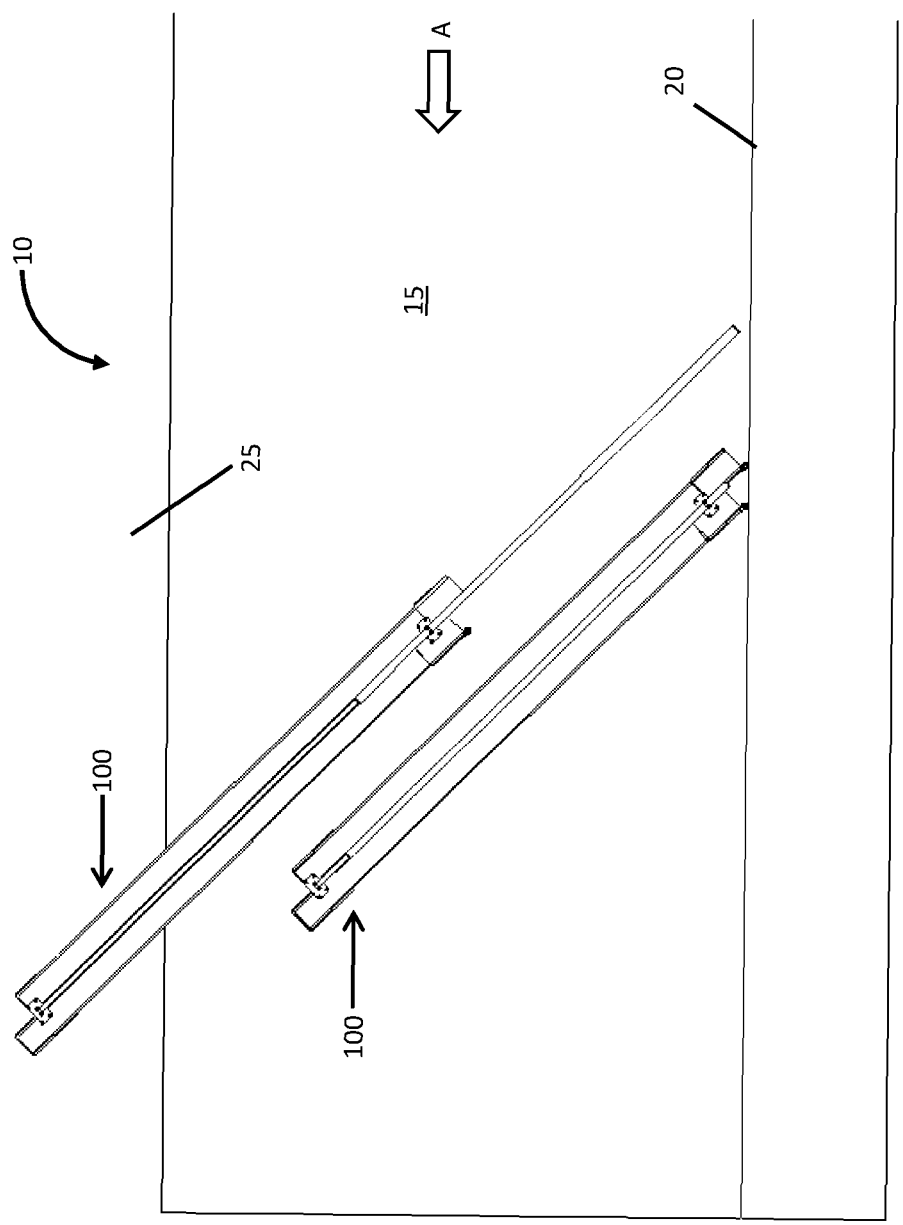
FIG. 1 illustrates a side sectional view of a fluid treatment system incorporating a first embodiment of a present radiation source module.

In one of its aspects, the present invention relates to a radiation source module for use in a fluid treatment system, the radiation source module comprising: a plurality of elongate radiation source elements secured to a frame element, each elongate radiation source element having a longitudinal axis; a first motive element secured to a first side portion of the frame element; a second motive element secured to a second side portion of the frame element; wherein the first motive element and the second motive element are configured to reversibly translate the plurality of elongate radiation source elements in a direction substantially parallel to the longitudinal axis.

Preferred embodiments of this radiation source module may include any one or a combination of any two or more of any of the following features:

the first motive element is a first hydraulic motive element;
the first motive element is a first pneumatic motive element;
the first motive element is a first mechanical motive element;
the first motive element is a first screw-drive motive element;
the first motive element is a first chain-drive motive element;
the first motive element is a first rodless cylinder motive element;
the second motive element is a second hydraulic motive element;
the second motive element is a second pneumatic motive element;
the second motive element is a second mechanical motive element;
the second motive element is a second screw-drive motive element;
the second motive element is a second chain-drive motive element;
the second motive element is a second rodless cylinder motive element;
the frame element comprises a first side frame element movably coupled to the first motive element;
the frame element comprises a second side frame element movably coupled to the second motive element;
the frame element comprises a first side frame element movably coupled to the first motive element and a second side frame element movably coupled to the second motive element;
the frame element further comprises a bottom frame element interconnecting the first side frame element and the second side frame element;
the frame element further comprises a top frame element interconnecting the first side frame element and the second side frame element;
the module further comprises a plurality of frame elements, each of the frame elements have secured thereto a plurality of elongate radiation source elements, each elongate radiation source element have a longitudinal axis;
each frame element has secured to the first side portion thereof the first motive element;
each frame element has secured to the first side portion thereof the second motive element;
each frame element has secured to the first side portion thereof the first motive element and to the second side portion the second motive element;
less than each frame element has secured to the first side portion thereof the first motive element;
less than each frame element has secured to the first side portion thereof the second motive element;
less than each frame element has secured to the first side portion thereof the first motive element and to the second side portion the second motive element
only two frame elements have secured to the first side portion thereof the first motive element;
only two frame elements have secured to the first side portion thereof the second motive element;
only two frame elements have secured to the first side portion thereof the first motive element and to the second side portion the second motive element;
only a single frame element has secured to the first side portion thereof the first motive element;
only a single frame element has secured to the first side portion thereof the second motive element;
only a single frame element has secured to the first side portion thereof the first motive element and to the second side portion the second motive element;

the module further comprises a coupling element configured to secure an adjacent pair of frame elements such that actuation of the first motive element and the second motive element causes translation of the frame pair of frame elements in a direction substantially parallel to the longitudinal axis;

the module further comprises a first pair of coupling elements configured to secure the first side portion of an adjacent pair of frame elements such that actuation of the first motive element and the second motive element causes translation of the frame pair of frame elements in a direction substantially parallel to the longitudinal axis.

the module further comprises a second pair of coupling elements configured to secure the second side portion of an adjacent pair of frame elements such that actuation of the first motive element and the second motive element causes translation of the pair of frame elements in a direction substantially parallel to the longitudinal axis;

the module further comprises: (i) a first pair of coupling elements configured to secure the first side portion of an adjacent pair of frame elements such that actuation of the first motive element and the second motive element causes translation of the pair of frame elements in a direction substantially parallel to the longitudinal axis, and (ii) a second first pair of coupling elements configured to secure the second side portion of an adjacent pair of frame elements such that actuation of the first motive element and the second motive element causes translation of the pair of frame elements in a direction substantially parallel to the longitudinal axis;

each elongate radiation source element comprises a radiation source;

the radiation source is disposed in a protective sleeve;

the protective sleeve comprises a closed end and an open end;

each radiation source assembly comprises an ultraviolet radiation source; and/or each radiation source assembly comprises a low pressure high output ultraviolet radiation source.

With reference to FIG. 1, there is illustrated a fluid treatment system 10 comprising an open channel 15. Open channel 15 comprises a floor 20 and a pair of sidewalls 25. For clarity, only one of sidewalls 25 is shown in FIG. 1. Disposed in open channel 10 is a pair of radiation source modules 100, which will be described in more detail with reference to FIGS. 2-7. As illustrated, in use, fluid (e.g., water) flows in the direction of arrow A (those of skill in the art will understand that it is also possible to have fluid (e.g., water) flowing in the reverse direction of arrow A).

As can be seen in FIG. 1, the upstream radiation source module 100 is shown with the frame elements thereof retracted from the in use position. This allows for servicing of the radiation source elements in radiation source module 100. As further illustrated in FIG. 1, the downstream radiation source module 100 is shown in an in use position.

Figure 2:
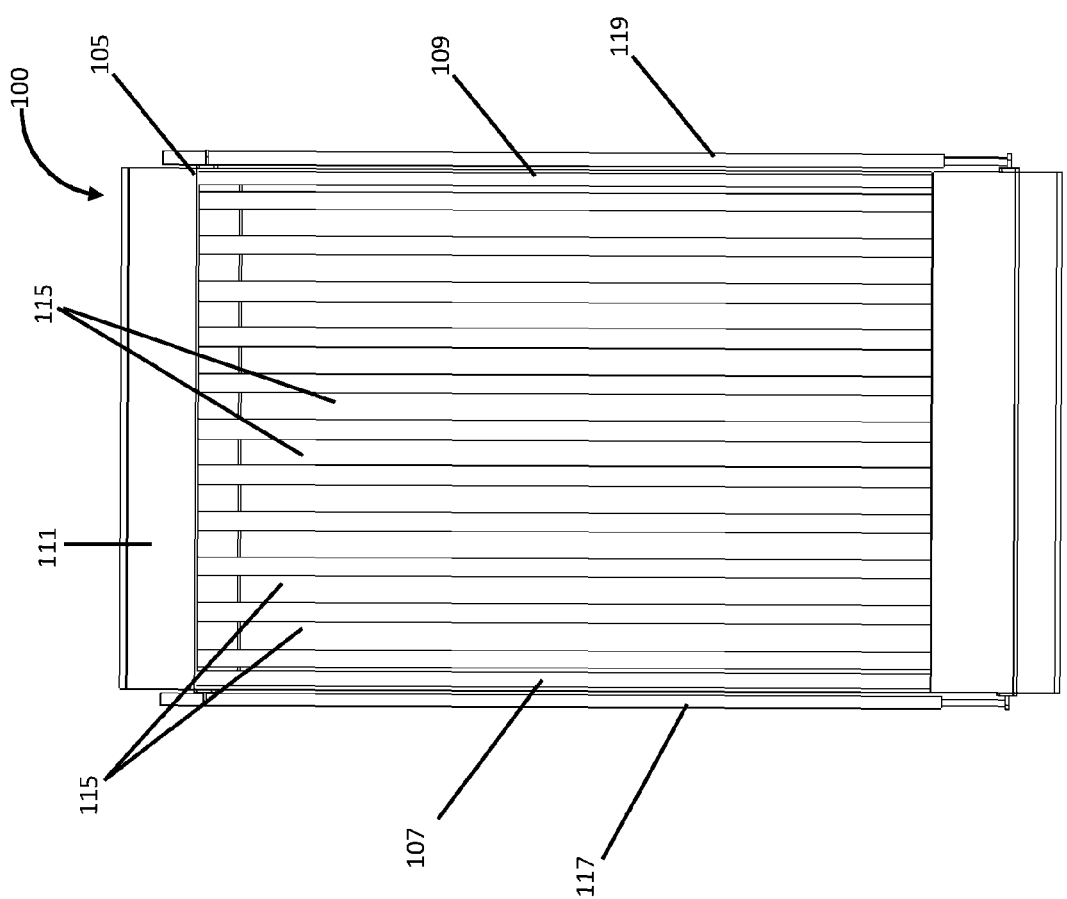
FIG. 2 illustrates a front view of a first embodiment of the present radiation source module.
Figure 4:
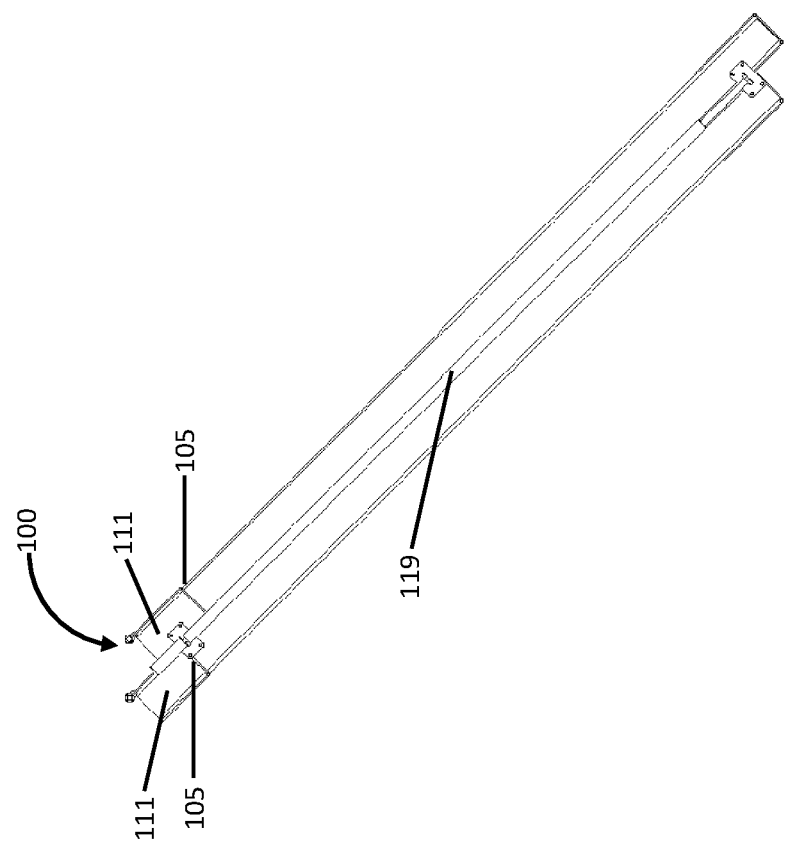
FIGS. 4-7 illustrate various side elevations of the radiation source module illustrated in FIGS. 2 and 3.
Figure 3:
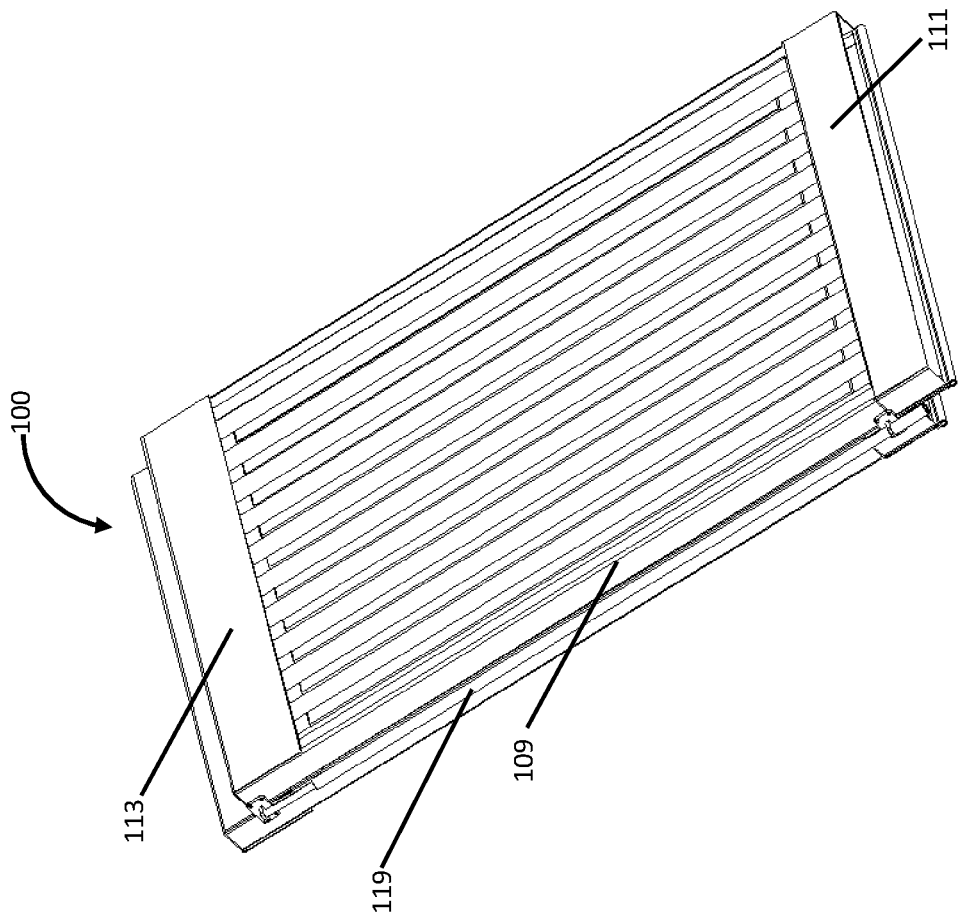
FIG. 3 illustrates a perspective view of the radiation source module illustrated in FIG. 2.

With reference to FIGS. 2-4, there is illustrated radiation source module 100. Radiation source comprises a pair of frame elements 105. Each frame element 105 comprises a pair of side frame elements 107,109 interconnected by a top frame element 111 and a bottom frame element 113. Disposed in each frame element 105 is a plurality of elongate radiation source elements 115. Each radiation source element 115 comprises an elongate radiation source such as an ultraviolet radiation source.

A first drive element 117 is secured to a side portion of frame element 105 adjacent to side frame element 107. A second drive element 119 is secured to a side portion of frame element 105 adjacent to side frame element 109. As set out above, these drive elements may be hydraulic, pneumatic or mechanical in their design.

Figure 6:
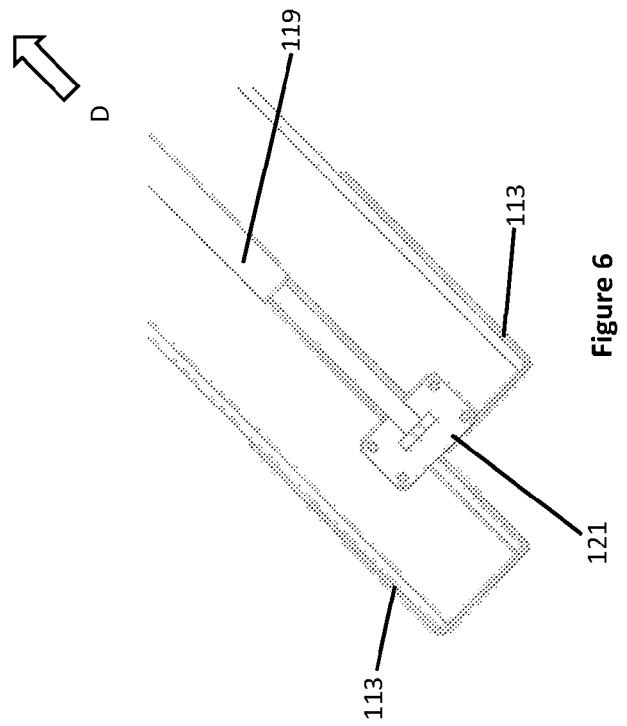
Figure 5:
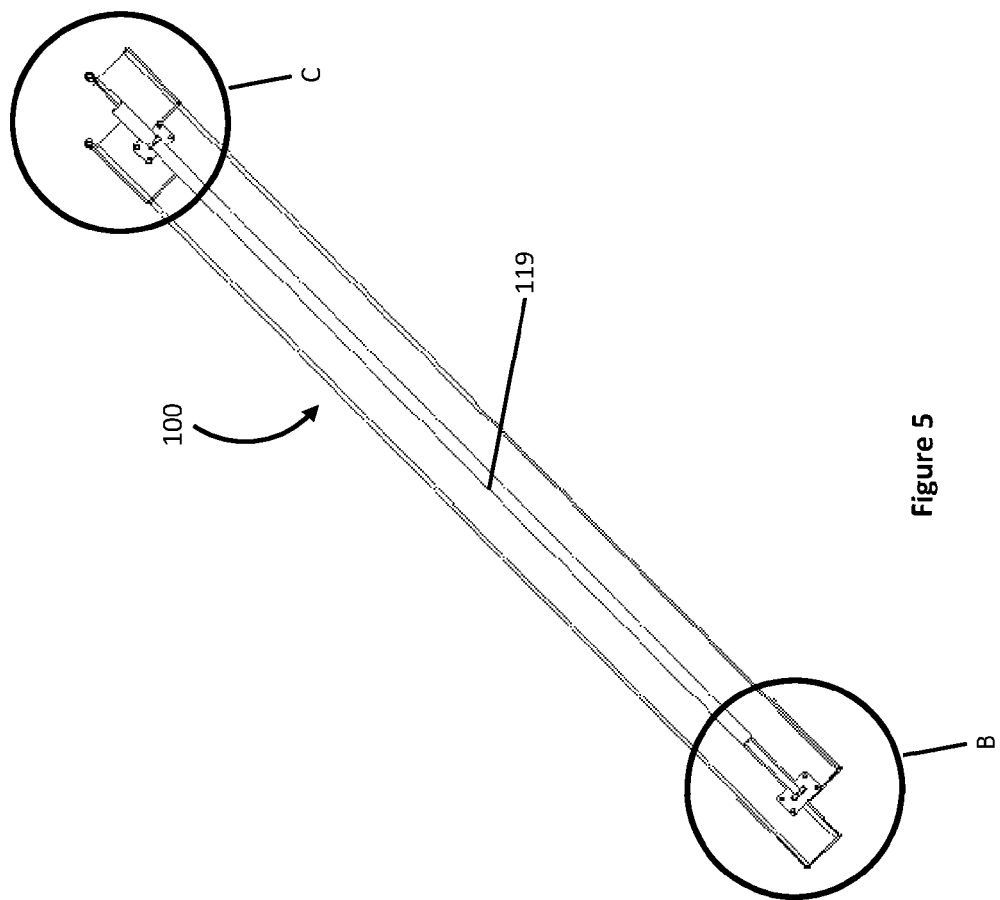
Figure 7:
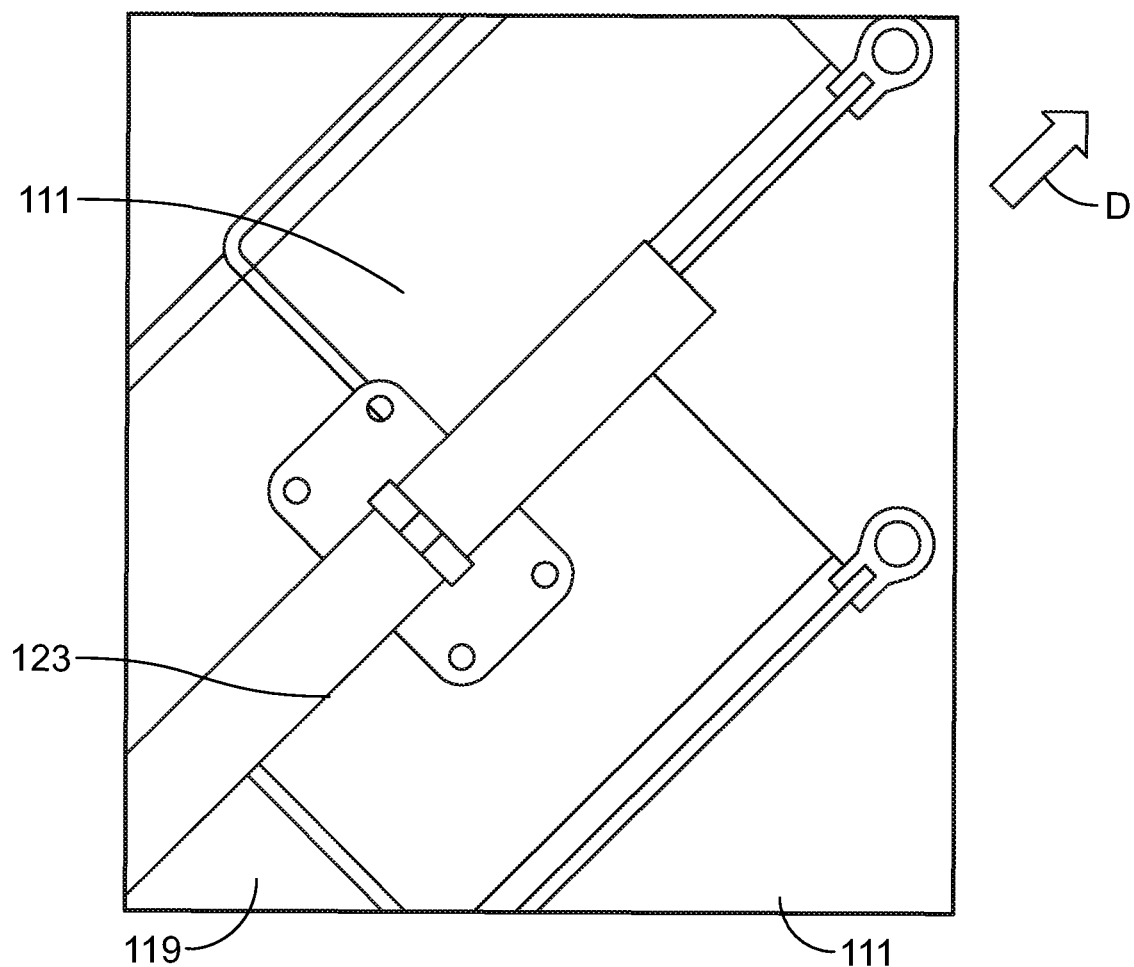

With reference to FIGS. 5-7, additional detail is provided on the interaction of drive elements 117, 119 and frame element 105 (for clarity, the focus will be on drive element 119).

FIG. 6 represents an enlarged portion of circle B in FIG. 5 while FIG. 7 illustrates an enlarged portion of circle C in FIG. 5.

As illustrated, a first coupling plate 121 is secured to each bottom frame element 113 of each frame element 105. Coupling plate 121 is also secured to drive element 119. A second coupling plate 123 is secured to top frame element 111 of frame element 105.

Drive element 119 is configured to be actuated in a direction of arrow D shown in FIGS. 6-7. When this occurs, the pair of frame elements 105 in radiation source module 100 is retracted as shown in the upstream radiation source module in FIG. 1. Once retracted, the radiation source element in frame element 105 may be serviced and thereafter returned to an in use position by reversibly actuating drive elements 117, 119.

Figure 8:
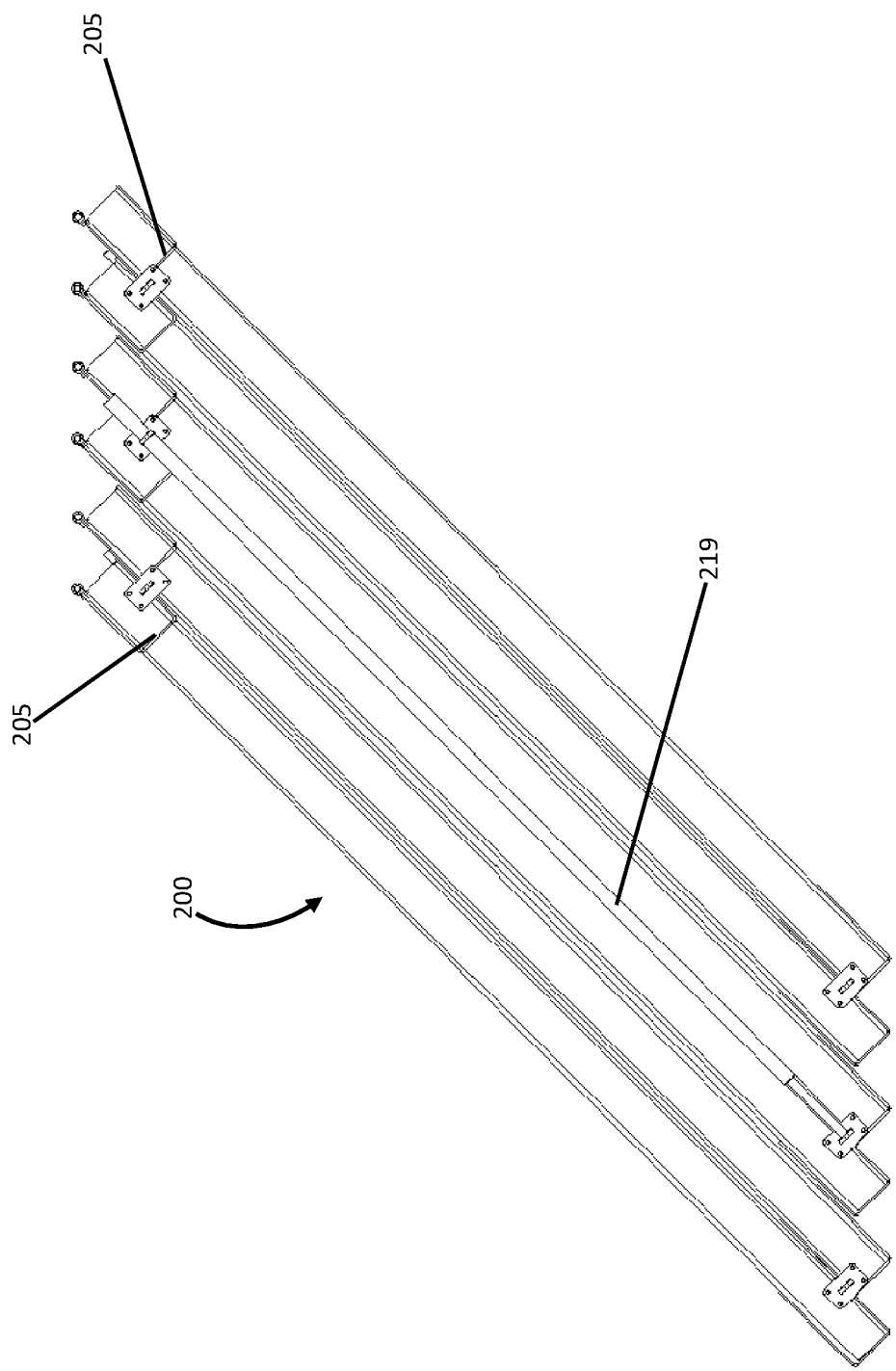
FIG. 8 illustrates a second embodiment of the present radiation source module.

With reference to FIG. 8, there is illustrated a modified embodiment of the radiation source module illustrated in FIGS. 1-7.

FIG. 8 illustrates a radiation source module 200 comprising a total of six (6) frames 205. Each frame 205 is of a similar design and construction of frame 105 in radiation source module 100 illustrated in FIGS. 1-7. The principal difference between radiation source module 100 illustrated in FIGS. 1-7 and radiation source module illustrated in FIG. 8 is that the six (6) frames in the latter are retracted with a single pair of drive elements (only drive element 219 is illustrated in FIG. 8 for clarity but it will be understood that a second drive element 217 would be disposed on the opposite side of radiation source module 200).

As shown drive element 219 is disposed between the middle pair of frame elements 205. The two outer pairs of frame elements 205 are secured to the middle pair of frame elements 205 by any suitable means (e.g., additional coupling plates, etc.). In the result, when the pair of drive elements in radiation source module is actuated, all six (6) frame elements 205 are retracted.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. For example, while the motive element of motive elements shown in the illustrated embodiments include a pneumatic, hydraulic, or mechanical device (such as winch), it is possible to modify these embodiments so that the module extraction device is human powered. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A radiation source module for use in a fluid treatment system, the radiation source module comprising:
   a plurality of elongate radiation source elements secured to a frame element, each of the plurality of elongate radiation source elements having a longitudinal axis;
   a first motive element secured to a first side portion of the frame element; and
   a second motive element secured to a second side portion of the frame element;
   wherein the first motive element and the second motive element are configured to reversibly translate the plurality of elongate radiation source elements in a direction substantially parallel to the longitudinal axis.

2. The radiation source module defined in claim 1, wherein the first motive element is a first hydraulic motive element.

3. The radiation source module defined in claim 1, wherein the first motive element is a first pneumatic motive element.

4. The radiation source module defined in claim 1, wherein the first motive element is a first mechanical motive element.

5. The radiation source module defined in claim 1, wherein the first motive element is a first rodless cylinder motive element.

6. The radiation source module defined in claim 1, wherein the second motive element is a second hydraulic motive element.

7. The radiation source module defined in claim 1, wherein the second motive element is a second pneumatic motive element.

8. The radiation source module defined in claim 1, wherein the second motive element is a second mechanical motive element.

9. The radiation source module defined in claim 1, wherein the second motive element is a second rodless cylinder motive element.

10. The radiation source module defined in claim 1, wherein the frame element comprises a first side frame element movably coupled to the first motive element and a second side frame element movably coupled to the second motive element.

11. The radiation source module defined in claim 10, wherein the frame element further comprises a bottom frame element interconnecting the first side frame element and the second side frame element.

12. The radiation source module defined in claim 10, wherein the frame element further comprises a top frame element interconnecting the first side frame element and the second side frame element.

13. The radiation source module defined in claim 1, comprising a plurality of frame elements, each of the plurality of frame elements have secured thereto a plurality of elongate radiation source elements, each of the plurality of elongate radiation source elements having a longitudinal axis.

14. The radiation source module defined in claim 13, wherein each of the plurality of frame elements has secured to the first side portion thereof the first motive element and to the second side portion the second motive element.

15. The radiation source module defined in claim 13, wherein less than each of the plurality of frame elements has secured to the first side portion thereof the first motive element and to the second side portion the second motive element.

16. The radiation source module defined in claim 13, wherein only two of the plurality of frame elements have secured to the first side portion thereof the first motive element and to the second side portion the second motive element.

17. The radiation source module defined in claim 13, wherein only one of the plurality of frame elements has secured to the first side portion thereof the first motive element and to the second side portion the second motive element.

18. The radiation source module defined in claim 16, further comprising a coupling element configured to secure an adjacent pair of frame elements such that actuation of the first motive element and the second motive element causes translation of the frame pair of frame elements in a direction substantially parallel to the longitudinal axis.

19. The radiation source module defined in claim 16, further comprising a first pair of coupling elements configured to secure the first side portion of an adjacent pair of frame elements such that actuation of the first motive element and the second motive element causes translation of the frame pair of frame elements in a direction substantially parallel to the longitudinal axis.

20. The radiation source module defined in claim 16, further comprising a second pair of coupling elements configured to secure the second side portion of an adjacent pair of frame elements such that actuation of the first motive element and the second motive element causes translation of the pair of frame elements in a direction substantially parallel to the longitudinal axis.

21. The radiation source module defined in claim 16, further comprising: (i) a first pair of coupling elements configured to secure the first side portion of an adjacent pair of frame elements such that actuation of the first motive element and the second motive element causes translation of the pair of frame elements in a direction substantially parallel to the longitudinal axis, and (ii) a second first pair of coupling elements configured to secure the second side portion of an adjacent pair of frame elements such that actuation of the first motive element and the second motive element causes translation of the pair of frame elements in a direction substantially parallel to the longitudinal axis.

22. A fluid treatment system comprising:
   an open channel for receiving a flow of fluid; and
   at least one radiation source module disposed in the open channel;
      wherein said at least one radiation source module comprises (i) a plurality of elongate radiation source elements secured to a frame element, each of the plurality of elongate radiation source elements having a longitudinal axis, (ii) a first motive element secured to a first side portion of the frame element, and (iii) a second motive element secured to a second side portion of the frame element;
      wherein the first motive element and the second motive element are configured to reversibly translate the plurality of elongate radiation source elements in a direction substantially parallel to the longitudinal axis.

* * * * *